(12) United States Patent
Takeuchi et al.

(10) Patent No.: US 10,624,991 B2
(45) Date of Patent: Apr. 21, 2020

(54) THREE-DIMENSIONAL ARTIFICIAL TISSUE, METHOD FOR PRODUCING THE SAME, THREE-DIMENSIONAL ARTIFICIAL TISSUE PERFUSION DEVICE, AND DRUG EVALUATION METHOD USING THREE-DIMENSIONAL ARTIFICIAL TISSUE

(71) Applicant: The University of Tokyo, Tokyo (JP)

(72) Inventors: Shoji Takeuchi, Tokyo (JP); Yuya Morimoto, Tokyo (JP); Nobuhito Mori, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 180 days.

(21) Appl. No.: 15/509,337

(22) PCT Filed: Jun. 30, 2015

(86) PCT No.: PCT/JP2015/068793
§ 371 (c)(1),
(2) Date: Mar. 7, 2017

(87) PCT Pub. No.: WO2016/047230
PCT Pub. Date: Mar. 31, 2016

(65) Prior Publication Data
US 2017/0274121 A1 Sep. 28, 2017

Related U.S. Application Data

(60) Provisional application No. 62/054,066, filed on Sep. 23, 2014.

(51) Int. Cl.
*C12M 3/00* (2006.01)
*A61L 27/36* (2006.01)
(Continued)

(52) U.S. Cl.
CPC ......... *A61L 27/362* (2013.01); *A61L 27/3679* (2013.01); *A61L 27/507* (2013.01);
(Continued)

(58) Field of Classification Search
CPC .................................................... C12M 21/08
See application file for complete search history.

(56) References Cited

U.S. PATENT DOCUMENTS

2010/0042120 A1* 2/2010 Hopkins ............... A61B 17/11
606/153
2011/0091926 A1* 4/2011 Frerich .................. C12M 21/08
435/29

FOREIGN PATENT DOCUMENTS

EP 2 203 553 A1 7/2010
EP 2 617 811 A1 7/2013
(Continued)

OTHER PUBLICATIONS

Miller et al., Nature Materials, 2012, vol. 11, p. 768-774.*
(Continued)

*Primary Examiner* — Jonathan M Hurst
(74) *Attorney, Agent, or Firm* — Westerman, Hattori, Daniels & Adrian, LLP

(57) ABSTRACT

The method for producing a three-dimensional artificial tissue is a method in which a three-dimensional artificial tissue extending in a predetermined direction is produced. The method includes: preparing a device including a culture tank having a culturing space surrounded by sidewalls, and a flow channel-forming member that penetrates through the sidewalls that face each other and is suspended in the culturing space along a predetermined direction; culturing cells in the culturing space and thereby forming a three-dimensional artificial tissue through which the flow channel-forming member penetrates; and removing the flow channel-forming member from the three-dimensional artificial tissue (Continued)

and thereby forming a perfusion flow channel that penetrates through the three-dimensional artificial tissue.

5 Claims, 13 Drawing Sheets

(51) Int. Cl.
*C12Q 1/02* (2006.01)
*C12M 1/00* (2006.01)
*C12M 1/12* (2006.01)
*A61L 27/50* (2006.01)
*A61L 27/60* (2006.01)
*A61L 27/00* (2006.01)

(52) U.S. Cl.
CPC ............. *A61L 27/60* (2013.01); *C12M 21/08* (2013.01); *C12M 23/04* (2013.01); *C12M 29/10* (2013.01); *C12Q 1/02* (2013.01); *A61L 27/00* (2013.01); *A61L 2430/22* (2013.01)

(56) References Cited

FOREIGN PATENT DOCUMENTS

| JP | 2005-518910 A | 6/2005 |
| JP | 2009-531067 A | 9/2009 |
| JP | 2010-539938 A | 12/2010 |
| JP | 2012-205516 A | 10/2012 |
| WO | 03/076604 A2 | 9/2003 |
| WO | 2007/112192 A2 | 10/2007 |
| WO | 2009/042418 A1 | 4/2009 |
| WO | 2009/042639 A2 | 4/2009 |

OTHER PUBLICATIONS

Supplementray European Search Report dated Apr. 4, 2018, issued in counterpart European Application No. 15844691.4. (15 pages).
Neumann et al., Tissue engineering of perfused microvessels, Microvascular Research, 2003, vol. 66, pp. 59-67 (9 pages), cited in ISR.
International Search Report dated Sep. 15, 2015, issued in counterpart International Application No. PCT/JP2015/068793 (2 pages).

* cited by examiner

THREE-DIMENSIONAL ARTIFICIAL TISSUE, METHOD FOR PRODUCING THE SAME, THREE-DIMENSIONAL ARTIFICIAL TISSUE PERFUSION DEVICE, AND DRUG EVALUATION METHOD USING THREE-DIMENSIONAL ARTIFICIAL TISSUE

The present invention relates to a three-dimensional artificial tissue, a method for producing the same, a three-dimensional artificial tissue perfusion device, and a method for evaluating a drug using a three-dimensional artificial tissue.

Priority is claimed on U.S. Provisional Patent Application No. 62/054,066, filed on Sep. 23, 2014, the content of which is incorporated herein by reference.

TECHNICAL FIELD

Background Art

Artificial skin tissues, a class of three-dimensional artificial tissues, are widely used for tests of cosmetics or pharmaceutics, skin transplantation, mounting in robots, and the like. Patent Document 1 discloses that coated cells having the surface coated with a coating film containing extracellular matrix components are cultured, and a dermal tissue layer in which coated cells are laminated is formed, and Patent Document 1 discloses a technology of producing an artificial skin model by disposing epidermal cells on a dermal tissue layer and thereby forming an epidermal layer.

CITATION LIST

Patent Literature

[PATENT DOCUMENT 1] Japanese Unexamined Patent Application, First Publication No. 2012-205516

SUMMARY OF INVENTION

Technical Problem

Culturing at a gas-liquid interface is essential for establishing an artificial skin tissue; however, in the culturing described in PATENT DOCUMENT 1, since a medium is supplied through a membrane filter disposed at a position that is remotest from the epidermal layer, it cannot be said that the efficiency of nutrient supply is sufficient, and for example, there is a possibility that a low quality artificial skin tissue having a low take ratio at the time of living donor organ transplantation may be produced.

The present invention was achieved in view of the problems described above, and it is an object of the invention to provide a high quality three-dimensional artificial tissue, a method for producing the same, a three-dimensional artificial tissue perfusion device, and a method for evaluating a drug using a three-dimensional artificial tissue.

Solution to Problem

According to a first aspect of the invention, there is provided a method for producing a three-dimensional artificial tissue extending in a predetermined direction, the method including: preparing a device that includes a culture tank having a culturing space surrounded by sidewalls, and a flow channel-forming member penetrating through the sidewalls that face each other and being suspended in the culturing space along the predetermined direction; forming the three-dimensional artificial tissue through which the flow channel-forming member penetrates by culturing cells in the culturing space; and removing the flow channel-forming member from the three-dimensional artificial tissue and thereby forming a perfusion flow channel that penetrates through the three-dimensional artificial tissue.

According to a second aspect of the invention, there is provided a method for evaluating a drug using a three-dimensional artificial tissue, the method including producing a three-dimensional artificial tissue by the production method according to the first aspect of the invention; bringing a drug into contact with the three-dimensional artificial tissue; and measuring the response of the three-dimensional artificial tissue to a stimulation caused by the contact with the drug.

According to a third aspect of the invention, there is provided a three-dimensional artificial tissue perfusion device in which perfusion to a three-dimensional artificial tissue extending in a predetermined direction is performed, the device including a culture tank having a culturing space surrounded by sidewalls; and a supporting portion that supports, in a freely attachable and detachable manner, a flow channel-forming member penetrating through the sidewalls that face each other and being suspended along the predetermined direction in a region where the three-dimensional artificial tissue is disposed in the culturing space.

According to a fourth aspect of the invention, there is provided a three-dimensional artificial tissue extending in a predetermined direction, the three-dimensional artificial tissue having a perfusion flow channel that penetrates through the interior of the tissue and extends in the predetermined direction.

Advantageous Effects of Invention

According to the invention, a high quality three-dimensional artificial tissue, a method for producing the same, a three-dimensional artificial tissue perfusion device, and a method for evaluating a drug using the three-dimensional artificial tissue can be provided.

DESCRIPTION OF EMBODIMENTS

In the following description, embodiments of the three-dimensional artificial tissue of the invention, a method for producing the same, a three-dimensional artificial tissue perfusion device, and a method for evaluating a drug using a three-dimensional artificial tissue will be explained with reference to FIG. 1 to FIG. 27.

The present embodiment will be explained using an example of producing an artificial skin tissue as a three-dimensional artificial tissue.

The following embodiments are intended to elicit one aspect of the invention. These embodiments are not intended to limit this invention, and can be arbitrarily modified within the scope of the technical idea of the invention. Furthermore, in the following drawings, the scales, numbers and the like in each of the structures will be indicated differently from those in the actual structures in order to help easy understanding of each configuration.

Artificial Skin Tissue

First, the artificial skin tissue according to the invention will be explained with reference to FIG. 1.

Figure 1:
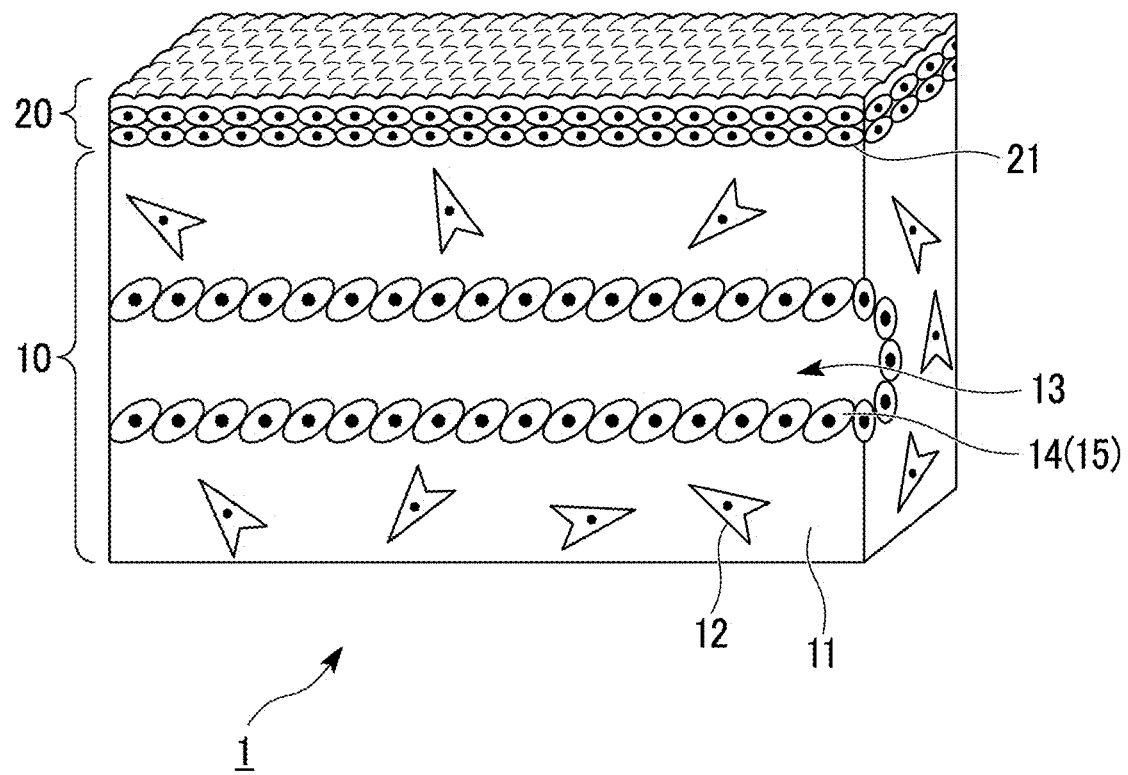
FIG. 1 is a perspective cross-sectional view schematically showing an artificial skin tissue 1 according to an embodiment of the invention.

FIG. 1 is a perspective cross-sectional view schematically showing an artificial skin tissue 1, which is a three-dimensional artificial tissue. The artificial skin tissue 1 includes a dermal tissue layer 10 and an epidermal layer 20. The artificial skin tissue 1 is formed so as to extend in a predetermined direction (horizontal direction in FIG. 1; hereinafter, referred to as first direction) along a plane that orthogonally intersects the direction in which the dermal tissue layer 10 and the epidermal layer 20 are laminated (vertical direction in FIG. 1; hereinafter, referred to as direction of lamination).

The epidermal layer 20 is a layer formed by inoculating and culturing epidermal cells 21 on the dermal tissue layer 10. Regarding the epidermal cells 21, for example, epidermal keratinocytes can be used.

Examples of the epidermal cells include cells derived from mammals such as a human being, a mouse, and a rat, and human-derived epidermal cells are preferred. Examples of the human-derived epidermal cells include epidermal keratinocytes and epidermal melanocytes, and epidermal keratinocytes are preferred. The epidermal keratinocytes may be normal human epidermal keratinocytes (NHEK). The epidermal melanocytes may be normal human epidermal melanocytes (NHEM).

The dermal tissue layer 10 is a layer formed by culturing dermal cells 12 in extracellular matrix components 11. The extracellular matrix components 11 are not particularly limited; however, examples thereof include collagens (type I, type II, type III, type V, type XI, and the like), basement membrane components reconstituted from a mouse EHS tumor extract (including type IV collagen, laminin, heparan sulfate proteoglycans, and the like) (trade name: MATRIGEL), gelatin, agar, agarose, fibrin, glycosaminoglycans, hyaluronic acid, and proteoglycans. Regarding the dermal cells 12, for example, fibroblasts can be used.

Examples of the fibroblasts include cells derived from mammals such as a human being, a mouse, a rat, and the like, and human-derived fibroblasts are preferred. Examples of the human-derived fibroblasts include human dermal fibroblasts (normal human dermal fibroblasts; NHDF), human pulmonary fibroblasts (HPF), human cardiac fibroblasts (HCF), human aortic adventitial fibroblasts (HAoAF), human uterine fibroblasts (HUF), and human villous mesenchymal fibroblasts (HVMF), and human dermal fibroblasts (NHDF) are preferred.

The dermal tissue layer 10 has perfusion flow channels 13 that penetrate through the interior of the dermal tissue layer 10 and extend in the first direction. A perfusion flow channel 13 is a flow channel through which a medium (details will be described below) is perfused when epidermal cells 21 are cultured. Provided on the surface of the perfusion flow channel 13 is a lumen layer 15 formed using vascular cells 14. Regarding the vascular cells 14, for example, endothelial cells can be used.

Examples of the vascular cells include vascular epithelial cells and vascular endothelial cells, and vascular endothelial cells are preferred. Examples of the vascular endothelial cells include cells derived from mammals such as a human being, a mouse, and a rat, and human-derived vascular endothelial cells are preferred. Examples of the human-derived vascular endothelial cells include human umbilical vein endothelial cells (HUVEC), human umbilical artery endothelial cells (HUAEC), human coronary artery endothelial cells (HCAEC), human saphenous vein endothelial cells (HSaVEC), human pulmonary artery endothelial cells (HPAEC), human aortic endothelial cells (HAoEC), human dermal microvascular endothelial cells (HDMEC), human dermal blood endothelial cells (HDBEC), human dermal lymphatic endothelial cells (HDLEC), human pulmonary microvascular endothelial cells (HPMEC), human cardiac microvascular endothelial cells (HCMEC), human bladder microvascular endothelial cells (HBdMEC), and human uterine microvascular endothelial cells (HUtMEC), and human umbilical vein endothelial cells (HUVEC) are preferred.

Artificial Skin Tissue Producing Apparatus

Next, an artificial skin tissue producing apparatus for producing the artificial skin tissue 1 described above will be explained with reference to FIG. 2 to FIG. 5.

Figure 2:
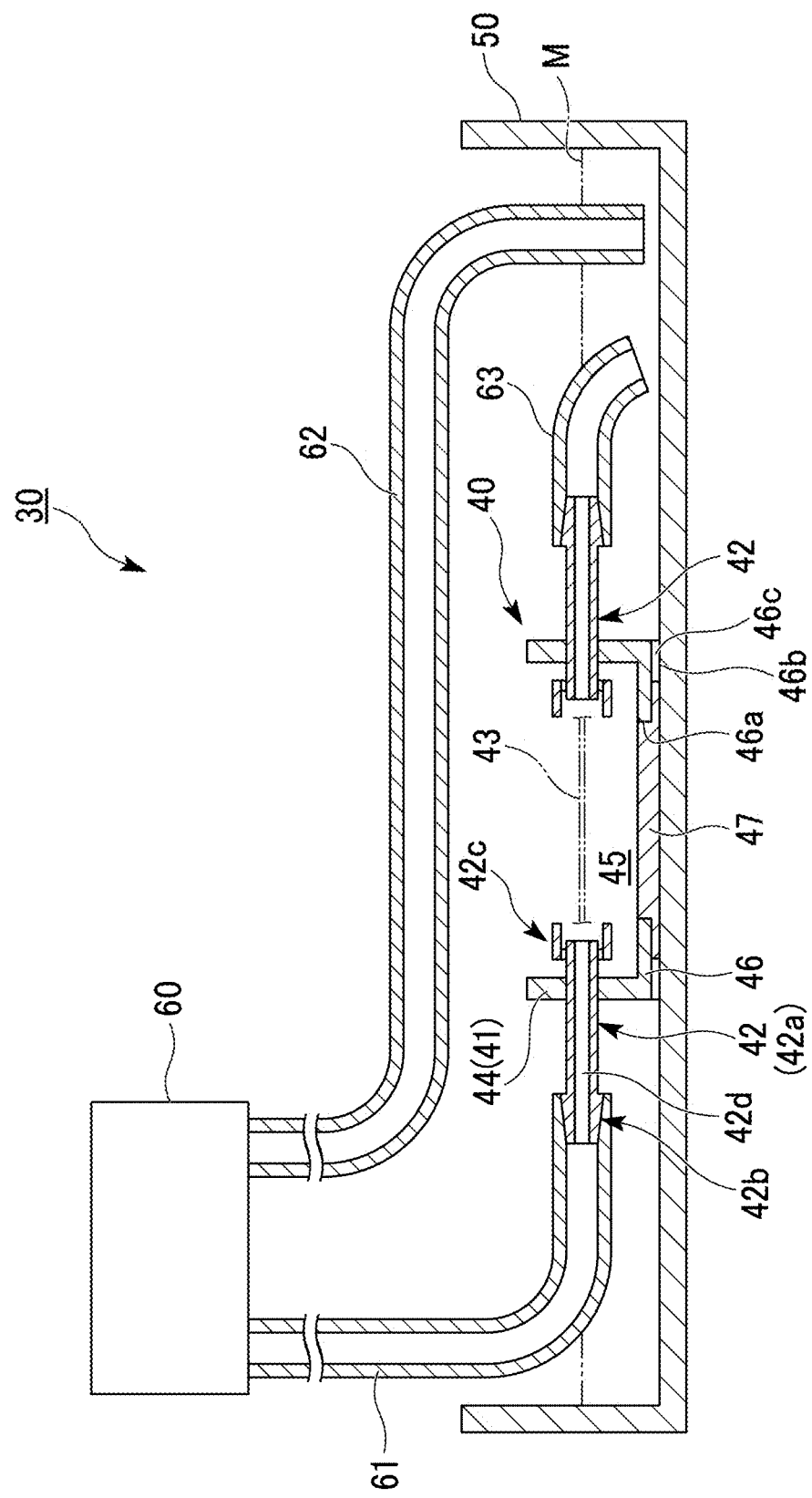
FIG. 2 is a schematic configuration diagram showing an artificial skin tissue production apparatus 30.

FIG. 2 is a schematic configuration diagram showing an artificial skin tissue producing apparatus 30.

The artificial skin tissue producing apparatus 30 includes a perfusion device (three-dimensional artificial tissue perfusion device) 40, a culture dish 50, and a pump 60. In the culture dish 50, the perfusion device 40 is placed in the internal space. The pump 60 supplies a medium to the perfusion device 40 through a pipe 61. The pump 60 collects a medium M that has been discharged into the culture dish 50 through the perfusion device 40, via a pipe 62.

First Embodiment of Perfusion Device 40

Figure 3:
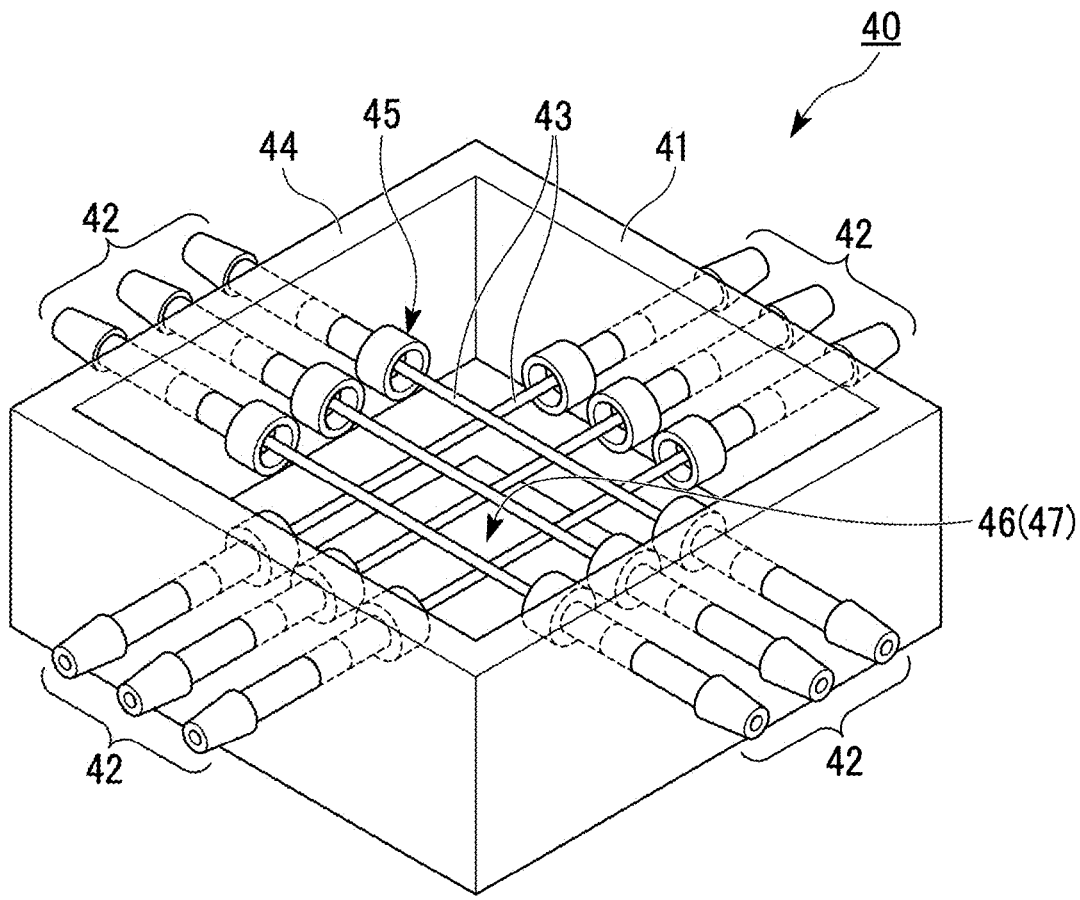
FIG. 3 is a perspective view of the external appearance of a first embodiment of a perfusion device 40.

FIG. 3 is a perspective view of the external appearance of a first embodiment of the perfusion device 40.

The perfusion device 40 includes a culture tank 41, connectors (supporting portions) 42, and wires (linear members, flow channel-forming members) 43. The culture tank 41 includes a culturing space 45 surrounded by sidewalls 44 with an open top; and a bottom plate 47 provided on a bottom wall (bottom) 46. The sidewalls 44 are provided in a rectangular form as viewed in a plan view. The bottom wall 46 has an opening 46a penetrating in a vertical direction; and a groove 46c provided on a bottom face 46b. The groove 46c is provided so as to extend in the first direction, and is open at the two ends toward the internal space of the culture dish 50. The bottom plate 47 is freely attachable and detachable from the culture tank 41. The bottom plate 47 blocks the opening 46a when mounted on the bottom wall 46 of the culture tank 41.

A connector 42 has a mounting portion (cylindrical portion) 42a, a connecting portion 42b, an engaging portion 42c, and a through-hole 42d that penetrates through the interior. The mounting portion 42a is formed in a shaft shape and is mounted so as to penetrate through the sidewalls 44 of the culture tank 41. The connecting portion 42b is provided at an end of the mounting portion 42a. The connecting portion 42b is disposed on the external side of the culture tank 41 and can be connected to the pipe 61 or the pipe 63 (will be described below).

Figure 4:
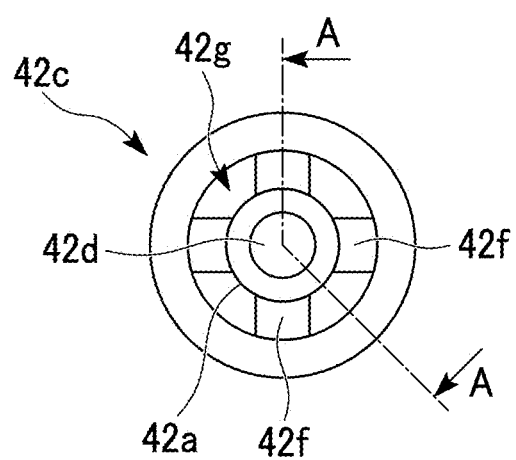
FIG. 4 is a diagram showing a front view of an engaging portion 42c viewed from the axial direction.
Figure 5:
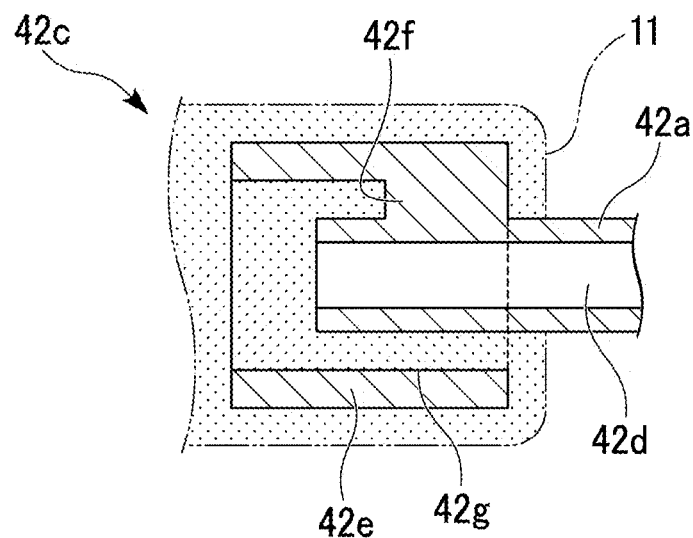
FIG. 5 is a cross-sectional view of FIG. 4 cut along the line A-A.

The engaging portion 42c is provided at the other end of the mounting portion 42a. The engaging portion 42c is disposed with a gap created between the engaging portion 42c and a sidewall 44 in the culturing space 45 of the culture tank 41. FIG. 4 is a diagram showing a front view of the engaging portion 42c as viewed from the axial direction. FIG. 5 is a cross-sectional view of FIG. 4 cut along the line A-A. As shown in FIG. 4 and FIG. 5, the engaging portion 42c includes a second cylindrical portion 42e coaxially disposed with a gap created between the second cylindrical portion 42e and the outer circumferential surface of the mounting portion 42a; and a plurality of rib portions 42f disposed at an interval in the circumferential direction of the mounting portion 42a. The rib portions 42f connect the outer circumferential surface of the mounting portion 42a and the inner circumferential surface of the second cylindrical portion 42e. There are four rib portions 42f provided at an interval of 90 degrees. A gap 42g surrounded by the mounting portion 42a, the second cylindrical portion 42e and the rib portions 42f penetrates through the engaging portion 42c in the axial direction.

A plurality of pairs of the connectors 42 (six pairs in FIG. 3) is mounted on the respective sidewalls 44 that face each other at positions where the through-holes 42d are coaxially disposed. Three pairs of connectors 42 are disposed along the first direction, and the other three pairs of connectors 42 are disposed along a second direction that orthogonally intersects the first direction in the horizontal direction. In a connector 42, at least a region that is exposed to the culturing space 45 should be subjected to a lyophilic treatment for the extracellular matrix components 11. Regarding the lyophilic treatment, for example, an $O_2$ plasma treatment can be employed.

A wire 43 is a linear member used for forming the perfusion flow channel 13. The wires 43 are supported, in a freely attachable and detachable manner, by the connectors 42 that are coaxially mounted on the sidewalls 44 that face each other. The wires 43 can be suspended in a region of the culturing space 45 where the dermal tissue layer 10 is disposed, by being inserted (supported) into the through-holes 42d of the connectors 42. The wires 43 are formed from, for example, a polyamide resin.

Method for Producing Artificial Skin Tissue 1

Next, a method for producing the artificial skin tissue 1 will be explained with reference to FIG. 6 to FIG. 20.

The method for producing the artificial skin tissue (three-dimensional artificial tissue) 1 according to the invention is a method for producing an artificial skin tissue 1 that has an epidermal layer 20 formed on a dermal tissue layer 10 and extends in a first direction (predetermined direction), the method including: preparing a perfusion device (three-dimensional artificial tissue perfusion device, device) 40 that includes a culture tank 41 having a culturing space 45 surrounded by sidewalls 44, and wires (linear members, flow channel-forming members) 43 penetrating through the sidewalls 44 that face each other and being suspended in the culturing space 45 along a predetermined direction; culturing dermal cells 12 in extracellular matrix components 11 in the culturing space 45 and thereby forming a dermal tissue layer 10 through which the wires 43 penetrate; removing the wires 43 from the dermal tissue layer 10 and thereby forming perfusion flow channels 13 that penetrate through the dermal tissue layer 10; disposing epidermal cells 21 on the dermal tissue layer 10, and forming an epidermal layer 20 while perfusing a medium M through the perfusion flow channels 13. Furthermore, the method for producing the artificial skin tissue 1 according to the invention includes engaging extracellular matrix components 11 with the engaging portions 42c respectively provided on the sidewalls 44 that face each other, and forming the dermal tissue layer 10 while suppressing shrinkage in the predetermined direction.

In the following description, the method for producing the artificial skin tissue 1 will be explained in detail.

In FIG. 6 to FIG. 20, only the perfusion device 40 is shown as appropriate, and illustration of the culture dish 50, the pump 60 and the like is omitted.

Preparation of Perfusion Device 40

Figure 6:
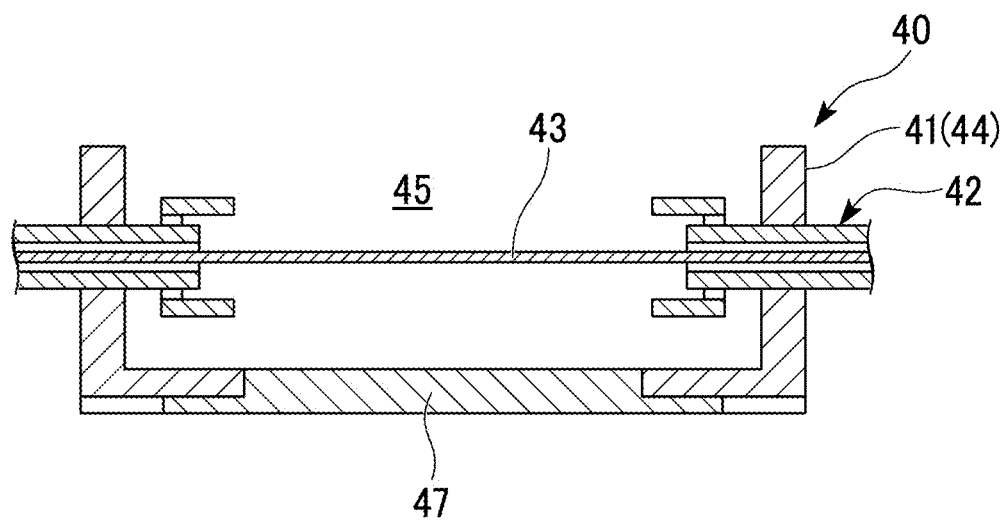
FIG. 6 is a diagram showing the production procedure of an artificial skin tissue 1.

Regarding the preparation of the perfusion device 40, as shown in FIG. 6, connectors 42 are mounted on the sidewalls 44 that face each other of the aforementioned culture tank 41 so as to be disposed coaxially with through-holes 42d, and also, openings 46a are blocked by attaching a bottom plate 47 to the bottom wall 46. Wires 43 are inserted into the through-holes 42d that are coaxially disposed, and the wires 43 are suspended in the culturing space 45.

Among the connectors 42, at least a region that is exposed to the culturing space 45 is subjected to a lyophilic treatment. The lyophilic treatment may be applied to the connectors 42 before the connectors are mounted in the culture tank 41, or may be applied to the connectors 42 that have been mounted on the sidewalls 44.

In order to seal the gap created by the mounting portion of the connector 42 with the sidewalls 44 and the gap created by the attaching portion of the bottom plate 47 with the bottom wall 46, the surface of the culture tank 41 that faces the culturing space 45 is coated with a sealing material. Regarding the sealing material, a film of a material that does not adversely affect the extracellular matrix components 11, the dermal cells 12 and the epidermal cells 21, for example, polyparaxylylene (hereinafter, referred to as PARYLENE), is formed by a film-forming method such as vapor deposition. The film thickness of the sealing material is preferably $1/100$ to $1/10$ with respect to the widths of the gap of the mounting portion and the gap of the attaching portion. The film thickness of the sealing material is preferably $1/50$ to $1/10$, and more preferably $1/50$ to $1/20$, with respect to the widths of the gap of the mounting portion and the gap of the attaching portion. In the present embodiment, a film of the sealing material is formed at a film thickness of 2 μm with respect to a gap having a width of about 50 μm ($1/25$).

Formation of Dermal Tissue Layer 10

When preparation of the perfusion device 40 is completed, a dermal tissue layer 10 is formed.

Figure 7:
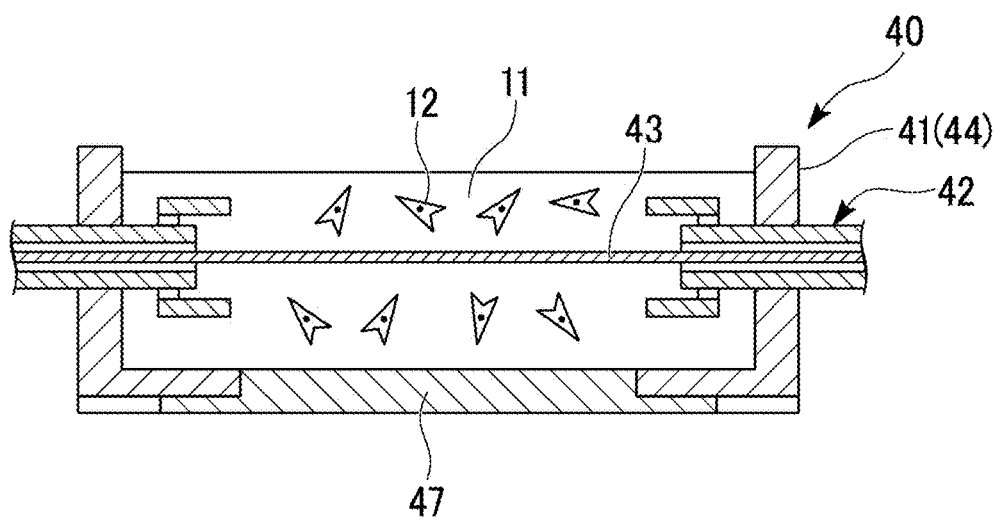
FIG. 7 is a diagram showing the production procedure of the artificial skin tissue 1.

Formation of the dermal tissue layer 10 is carried out by, first, as shown in FIG. 7, pouring a mixture of extracellular matrix components 11 and dermal cells 12 into the culturing space 45 of the culture tank 41. The mixture is poured in an amount that reaches a height causing the wires 43 to submerge therein. In the present embodiment, collagen is used as the extracellular matrix component 11.

When the mixture of extracellular matrix components 11 and dermal cells 12 is poured into the culture tank 41, the mixture is cultured (incubated) under predetermined conditions. Regarding the culturing conditions, culture is performed under the conditions in which the density of the dermal tissue layer 10 is equivalent to the density of human dermis. Regarding the culturing conditions, for example, culture was performed for 2 days (48 hours) at a temperature of 37° C.

The extracellular matrix components 11 shrink as a result of culture. Since the extracellular matrix components 11 are engaged at the engaging portion 42c, shrinkage in the direction of lamination is not constrained; however, shrinkage in the first direction and the second direction is constrained. More specifically, as shown in FIG. 5, since the extracellular matrix components 11 are engaged with the second cylindrical portion 42e and the rib portion 42f of the engaging portion 42c from the opposite side of the center of the culturing space 45, the second cylindrical portion 42e and the rib portion 42f serve as barriers, and shrinkage toward to the central side is suppressed. Furthermore, the extracellular matrix components 11 are pressure-bonded to the outer circumferential surface of the second cylindrical portion 42e and the outer circumferential surface on the tip side of the mounting portion 42a by shrinkage in the direction of lamination. Accordingly, the frictional force between the extracellular matrix components 11 and the engaging portion 42c is increased, and the resistive force against shrinkage in the first direction and the second direction increases. Particularly, according to the present embodiment, since the engaging portion 42c is subjected to a lyophilic treatment for the extracellular matrix components 11, the extracellular matrix components 11 closely adhere to the engaging portion 42c with a larger adhesive force, and the resistive force against shrinkage in the first direction and the second direction is increased.

Figure 8:
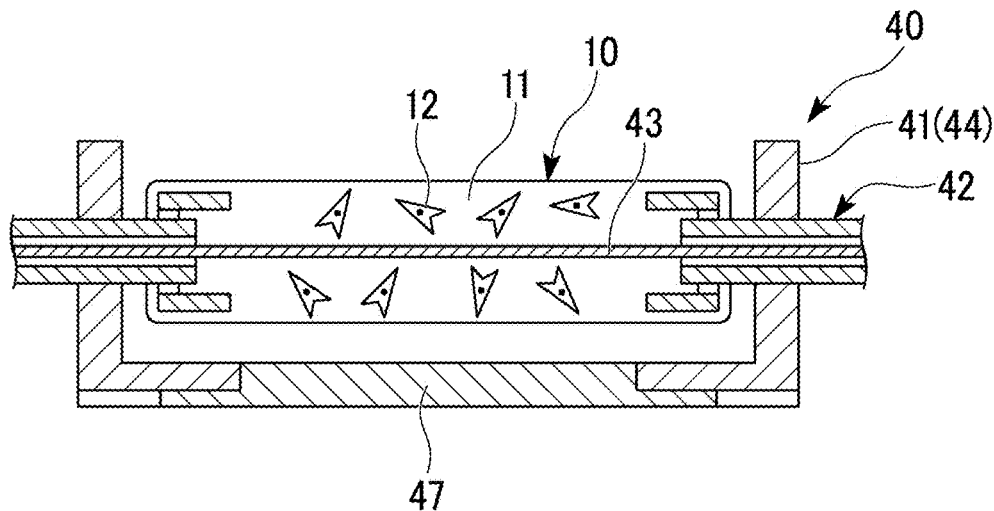
FIG. 8 is a diagram showing the production procedure of the artificial skin tissue 1.

As the culture of the mixture of extracellular matrix components 11 and dermal cells 12 is completed, as shown in FIG. 8, shrinkage occurs in the direction of lamination, while shrinkage in the first direction and the second direction is suppressed, and thus a dermal tissue layer 10 through which the wires 43 penetrate is formed.

Formation of Perfusion Flow Channels 13 and Lumen Layer 15

Figure 9:
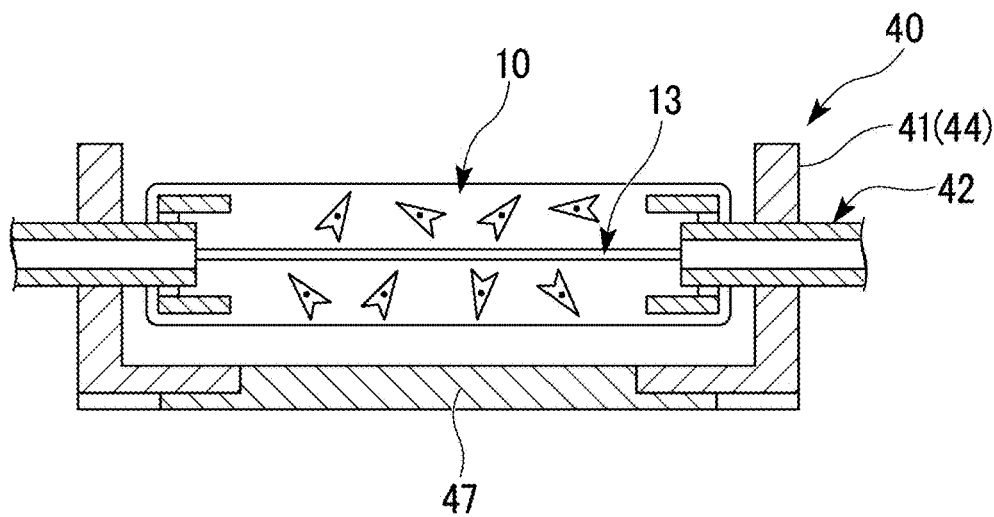
FIG. 9 is a diagram showing the production procedure of the artificial skin tissue 1.

Next, the wires 43 supported by the connectors 42 are removed. Thereby, as shown in FIG. 9, perfusion flow channels 13, which are cavities extending in the first direction, are formed in the dermal tissue layer 10. At this time, since the dermal tissue layer 10 is engaged with the engaging portions 42c at both ends, the dermal tissue layer 10 is stably supported by the connectors 42 without escaping from the connectors 42 at the time of removal of the wires 43.

Figure 10:
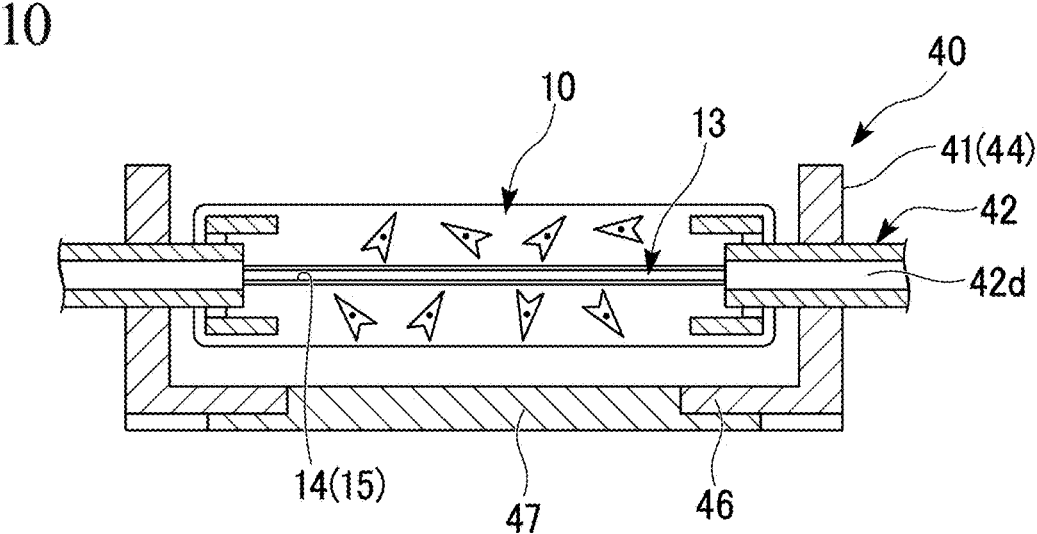
FIG. 10 is a diagram showing the production procedure of the artificial skin tissue 1.

Next, as shown in FIG. 10, a lumen layer 15 is formed by pouring (inoculating) vascular cells 14 onto the surface of the dermal tissue layer 10 facing the perfusion flow channels 13, through the through-holes 42d of the connectors 42, and culturing the vascular cells 14 for a certain period of time. Thereby, the perfusion flow channels 13 are in a state of being surrounded by the lumen layer 15.

Formation of Epidermal Layer 20

Next, preparation for forming an epidermal layer 20 is implemented.

Figure 11:
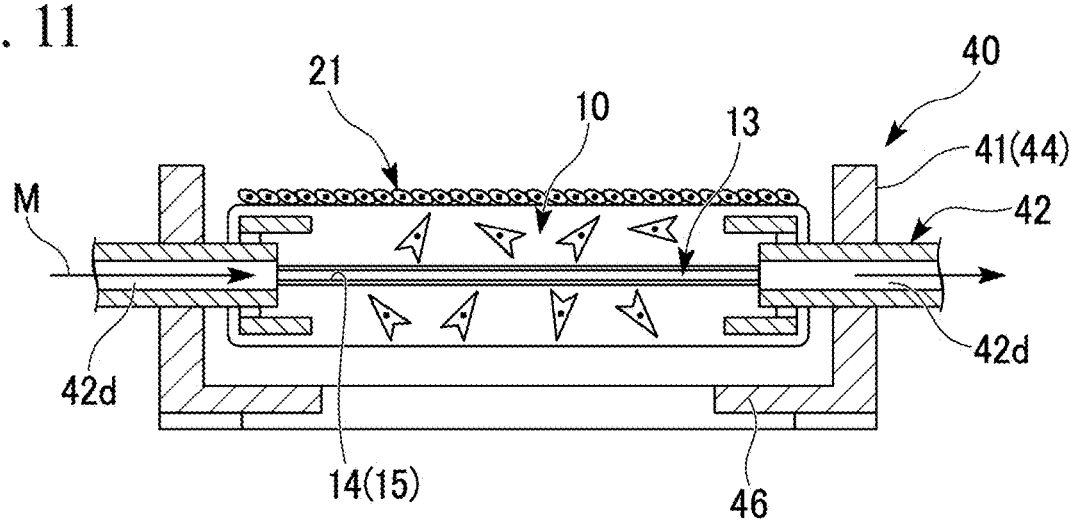
FIG. 11 is a diagram showing the production procedure of the artificial skin tissue 1.
Figure 12:
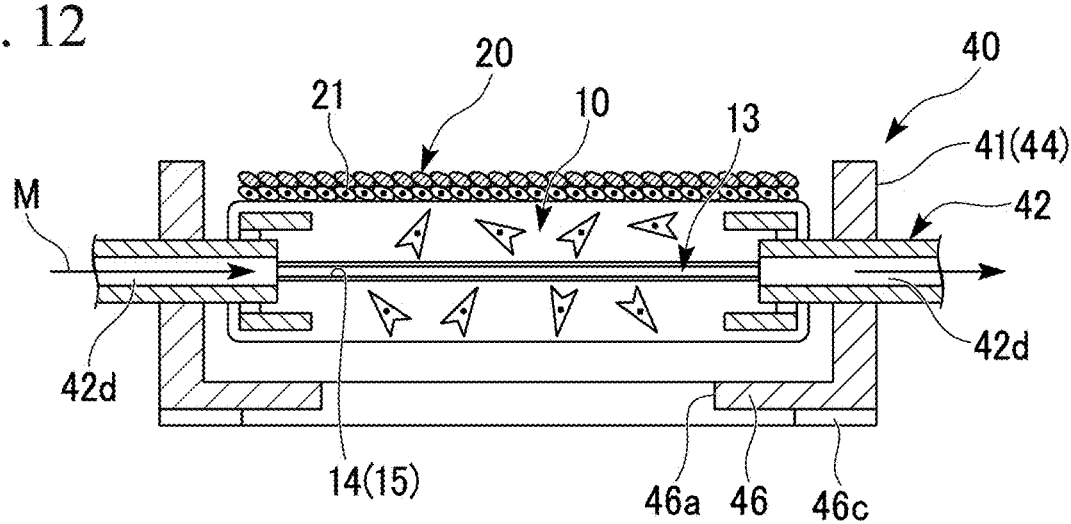
FIG. 12 is a diagram showing the production procedure of the artificial skin tissue 1.

As shown in FIG. 11, the bottom plate 47 is removed from the bottom wall 46 of the culture tank 41, and also, the culture tank 41 is placed inside the culture dish 50 as shown in FIG. 2. Next, pipe 61 is connected to the connecting portions 42b of the connectors 42 on one side of the first direction, and a pipe 63 is connected to the connecting portions 42b of the connectors 42 on the other side of the first direction. The pipe 61 or pipe 63 that is connected to the connecting portions 42b on each side may be connected to all of the three connectors 42, or may be connected to some of the connectors only.

When the preparation for forming the epidermal layer 20 is completed, epidermal cells 21 are inoculated on the dermal tissue layer 10. When the epidermal cells 21 are inoculated, the epidermal cells 21 are cultured while a medium M is perfused to the perfusion flow channels 13 through the pipe 61 and the through-holes 42d from the pump 60. Culture of the epidermal cells 21 is carried out by gas-liquid culture, in which the epidermal cells 21 are exposed to a gas while the medium M in the perfusion flow channels 13 are diffused through the dermal tissue layer 10.

Thereby, the epidermal cells 21 undergo induced differentiation, and thus, an epidermal layer 20 can be formed. Regarding the culturing conditions employed at the time of forming the epidermal layer 20, for example, culture was performed for 9 days at a temperature of 37° C.

The medium M that has been perfused to the perfusion flow channels 13 through the connectors 42 on one side is discharged into the internal space of the culture dish 50 through the connectors 42 on the other side and the pipe 63. Also, a portion of the medium M that has diffused into the dermal tissue layer 10 from the perfusion flow channels 13 is discharged into the internal space of the culture dish 50 through the opening 46a and the groove 46c of the culture tank 41. The medium M that has been discharged into the culture dish 50 is collected through the pipe 62. The amount of the medium M supplied from the pump 60 and the amount of the medium M collected through the pipe 62 are set to a value at which the liquid level of the medium M in the culture dish 50 is maintained such that the lower side of the dermal tissue layer 10 is immersed in the medium M at the time of the culture of the epidermal layer 20, and the epidermal cells 21 are exposed to air.

Evaluation Method

Another aspect of the invention relates to a method for evaluating skin irritancy of a drug using the artificial skin tissue 1 of the invention. Drugs according to the invention include a drug such as a pharmaceutical product, a cosmetic product, and a quasi-drug. According to the evaluation method of the invention, for example, evaluation of a drug can be carried out in an environment close to the actual skin, as compared to conventional methods. Furthermore, the evaluation method of the invention is very useful for, for example, a dynamic evaluation of drugs having various molecular weights in creation of new drugs (screening) or the like; and an evaluation in the development of cosmetic products, quasi-drugs and the like.

The evaluation method of the invention can be carried out by, for example, bringing a drug into contact with the artificial skin tissue, and measuring the response to a stimulation caused by the contact with the drug. Measurement of the response can be performed by, for example, measuring the transcutaneous electrical resistance. The drug may be any substance that serves as an object of evaluation, and examples thereof include an inorganic compound and an organic compound.

EXAMPLES

Figure 13:
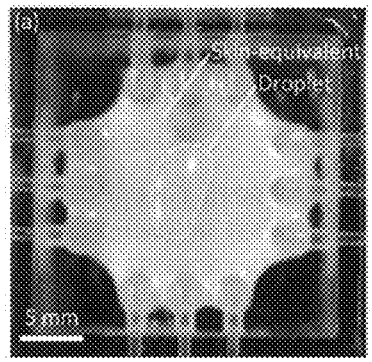
FIG. 13 is a diagram showing the artificial skin tissue 1 thus produced.

FIG. 13 is a diagram showing an artificial skin tissue 1 produced by the production method described above. As shown in this diagram, an artificial skin tissue 1 in a state in which shrinkage in the first direction and the second direction was suppressed by the connectors 42 was obtained.

Figure 14:
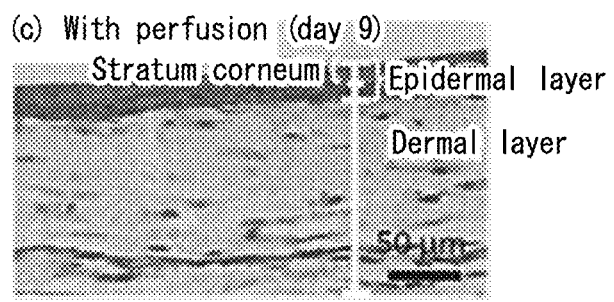
FIG. 14 is a diagram showing the results of producing the artificial skin tissue 1 by perfusing a medium M through perfusion flow channels 13.
Figure 15:
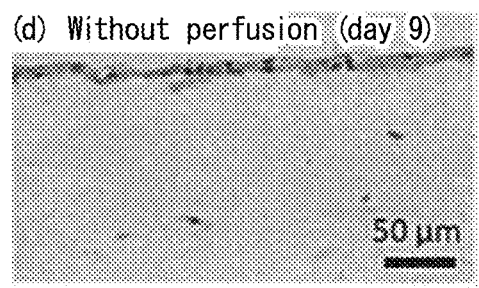
FIG. 15 is a diagram showing the results of producing the artificial skin tissue 1 without providing the perfusion flow channels 13.

FIG. 14 is a diagram showing the results of producing the artificial skin tissue 1 by perfusing the medium M through the perfusion flow channels 13. FIG. 15 is a diagram showing the results of producing the artificial skin tissue 1 without providing the perfusion flow channels 13. As shown in FIG. 14, in a case in which the medium M was perfused through the perfusion flow channels 13, the dermal tissue layer 10 and the epidermal layer 20 could be formed. However, as shown in FIG. 15, in a case in which the perfusion flow channels 13 were not provided, the epidermal layer 20 could not be formed.

Figure 16:
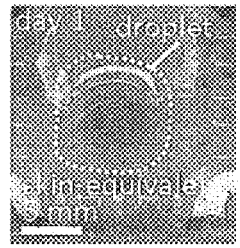
FIG. 16 is a diagram showing an epidermal layer 20 coated with a liquid droplet on the surface.
Figure 17:
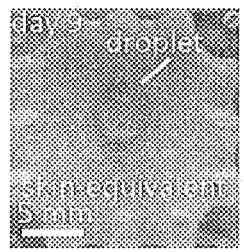
FIG. 17 is a diagram showing the epidermal layer 20 coated with a liquid droplet on the surface.

FIG. 16 is a diagram showing the epidermal layer 20 obtained after performing culture of the epidermal layer 20 for one day, the epidermal layer 20 having a liquid droplet applied on the surface. FIG. 17 is a diagram showing the epidermal layer 20 obtained after performing culture of the epidermal layer 20 for 9 days, the epidermal layer 20 having a liquid droplet applied on the surface. As shown in FIG. 16, the liquid droplet applied on the surface of the epidermal layer 20 wetted and spread largely on the surface in the case in which one day had passed after initiation of culture. However, as shown in FIG. 17, in the case in which 9 days had passed after initiation of culture, the wet spreading was reduced. That is, it is speculated that the surface of the epidermal layer 20 after a lapse of 9 days from the initiation of culture acquired increased liquid repellency, and thus keratinization of the stratum corneum had proceeded.

Figure 18:
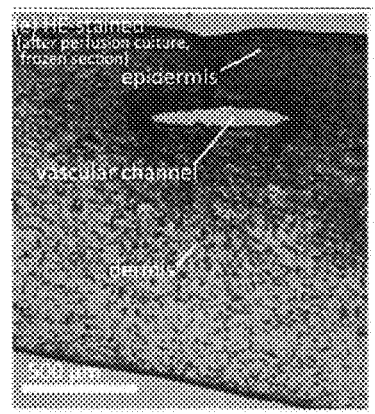
FIG. 18 is a diagram showing a cross-section of the artificial skin tissue 1 cut in the vertical direction.
Figure 19:
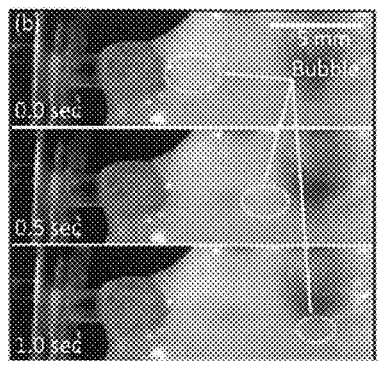
FIG. 19 is a diagram showing an observation made on air bubbles moving through the perfusion flow channels 13.

FIG. 18 is a diagram showing a cross-sectional view of the artificial skin tissue 1 in the vertical direction after a lapse of 9 days from the initiation of culture of the epidermal layer 20. As shown in FIG. 18, it could be confirmed that even in the case of a lapse of 9 days after the initiation of culture, the perfusion flow channels 13 were maintained FIG. 19 is a diagram showing an observation made on air bubbles moving through a perfusion flow channel 13 in the artificial skin tissue 1 after a lapse of 9 days from the initiation of culture. As shown in FIG. 19, it could be confirmed that air bubbles flowed as time passed, and it could be confirmed that the function of the perfusion flow channels 13 was maintained.

Figure 20:
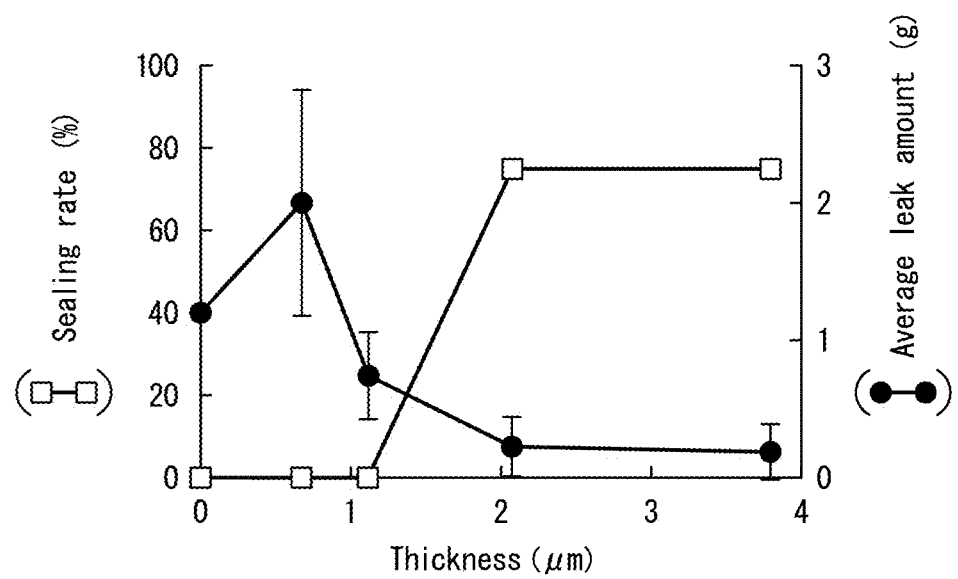
FIG. 20 is a diagram showing the sealing success ratio with respect to the thickness of the sealing material, and the average amount of extracellular matrix components 11 leaking through the gap of the attaching portion of the bottom plate 47.

FIG. 20 is a diagram showing, in connection with sealing of the gap of the mounting portions of the connectors 42 and the gap of the attaching portion of the bottom plate 47, the sealing success ratio with respect to the thickness of the sealing material and the average amount of the extracellular matrix components 11 leaking through the gap of the attaching portion of the bottom plate 47. As shown in FIG. 20, in the case of a gap having a width of 50 µm, a high sealing rate and a low average leak amount could be achieved by setting the thickness of the sealing material PARYLENE to 2 µm, which was ½5 of the gap width.

As explained above, in the present embodiment, since perfusion flow channels 13 that penetrate through the interior of the dermal tissue layer 10 are provided, sufficient supply of nutrients is enabled even when the epidermal layer 20 is formed. Therefore, in the present embodiment, a high quality artificial skin tissue 1 having a high take ratio at the time of living donor organ transplantation can be obtained. According to the present embodiment, the perfusion flow channels 13 can be formed easily by an operation of removing the wires 43, and the cost and efforts required for the production of the artificial skin tissue 1 can be reduced.

In the present embodiment, since the lumen layer 15 is provided on the surface that faces the perfusion flow channels 13, the perfusion flow channels 13 can be retained more stably even when culture is performed over a long period of time. In the present embodiment, since the dermal tissue layer 10 is formed while shrinkage in the first direction and the second direction is suppressed, even in a case in which shrinkage occurs to a large extent as in the case of culturing dermal cells 12 in extracellular matrix components 11, a high quality artificial skin tissue 1 can be produced stably by retaining the perfusion flow channels 13. According to the present embodiment, since a lyophilic treatment is applied to the engaging portions 42c of the connectors 42, adhesiveness of the extracellular matrix components 11 to the engaging portions 42c can be increased to a large extent, and the dermal tissue layer 10 can be formed in a more stabilized state while shrinkage is suppressed. According to the present embodiment, since the bottom plate 47 that is capable of blocking the openings 46a of the bottom of the culture tank 41 is freely attachable and detachable, when culturing the epidermal layer 20, the used medium M that has been polluted, which accumulates at the bottom of the culture tank 41, can be easily discharged into the culture dish 50.

Second Embodiment of Perfusion Device 40A

Subsequently, a second embodiment of the perfusion device 40A will be explained with reference to FIG. 21 to FIG. 27.

In these diagrams, elements that are identical with the constituent elements of the first embodiment illustrated in FIG. 1 to FIG. 20 will be assigned with the same reference numerals, and a description of the elements will be omitted or simplified.

The case of producing a planar artificial skin tissue 1 has been shown in the first embodiment; however, the second embodiment will be explained using an example of producing an artificial skin tissue 1 having a curved cross-sectional shape.

Figure 21:
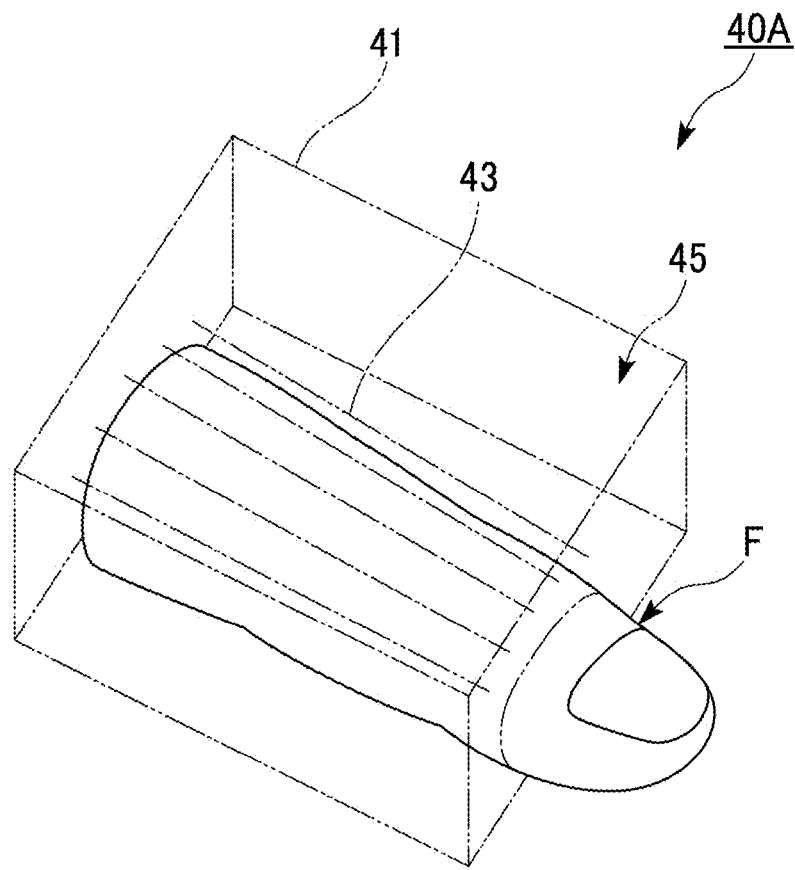
FIG. 21 is a schematic perspective view of a perfusion device 40A of a second embodiment.
Figure 22:
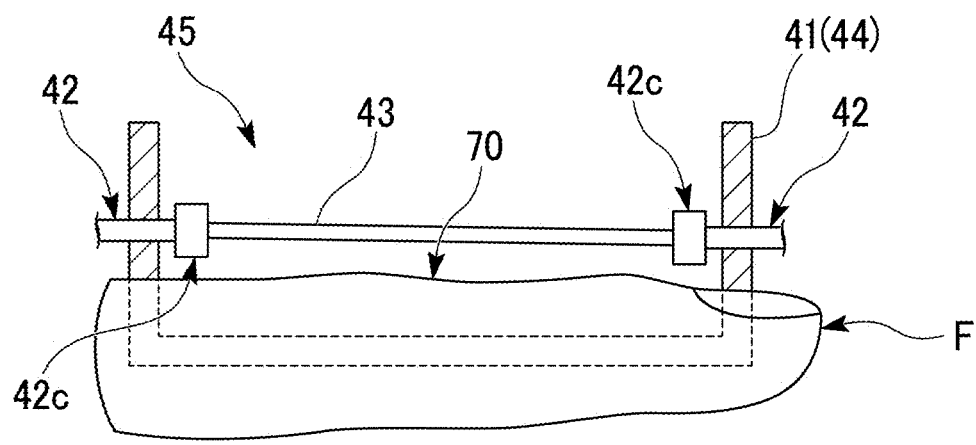
FIG. 22 is a diagram showing a cross-section of a biological model F cut at a vertical plane including the longitudinal direction.

FIG. 21 is a schematic perspective view of a perfusion device 40A in which a biological model F is provided in a culture tank 41. The biological model F is a model simulating a finger. FIG. 22 is a diagram illustrating a cross-sectional view of the biological model F cut at a vertical plane including the longitudinal direction (predetermined direction, first direction). FIG. 23 to FIG. 27 are diagrams illustrating a cross-sectional view of the biological model F cut at a plane orthogonally intersecting the longitudinal direction.

Figure 23:
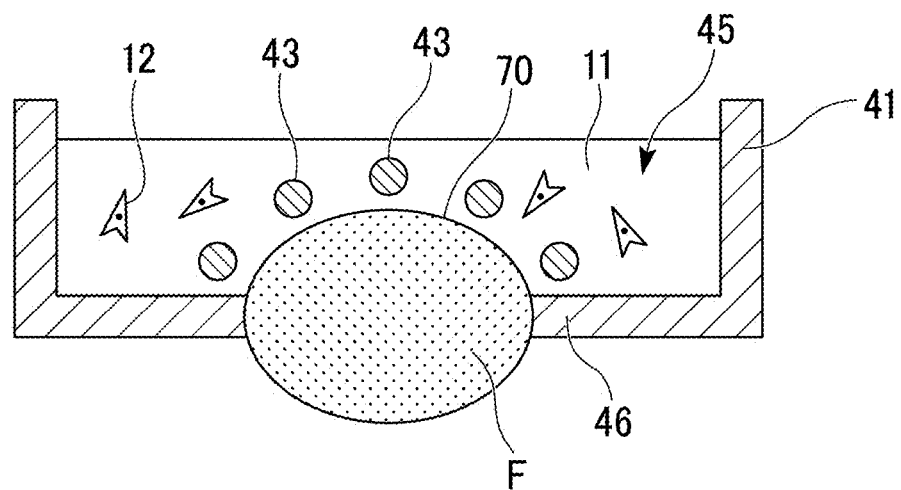
FIG. 23 is a diagram showing the production procedure of an artificial skin tissue 1 according to a second embodiment.

As shown in FIG. 22 and FIG. 23, the biological model F is such that the surface on the dorsal side is a curved surface 70, and the biological model F is provided from the bottom wall 46 of the culture tank 41 so as to be exposed to the culturing space 45. The joint between the bottom wall 46 of the culture tank 41 and the biological model F is sealed by PARYLENE mentioned above. Wires 43 are suspended along the gradient of the curved surface 70 in the first direction, such that the wire positions on the finger tip side are lower. As shown in FIG. 23, there is a plurality (five wires in FIG. 23) of wires 43 provided at an interval in the circumferential direction of the biological model F. The distance between each wire 43 and the biological model F is set to a distance at which a predetermined value of the thickness of the dermal tissue layer 10 formed between the wires 43 and the biological model F can be secured. The number of the wires 43 is determined as appropriate according to the width (length in the circumferential direction) of the epidermal layer 20.

Although not shown in FIG. 22 and FIG. 23, five connectors 42 (ten in total) are provided on the sidewalls 44 in accordance with the number of the wires 43. In the culture tank 41 of the present embodiment, the bottom plate 47 is not provided.

Other parts of the configuration are the same as those of the perfusion device 40 of the first embodiment.

Method for Producing Artificial Skin Tissue 1

Subsequently, a method for producing an artificial skin tissue 1 using the perfusion device 40A described above will be explained. Here, the explanation will be given under the assumption that preparation of the perfusion device 40A has been completed.

First, in order to form a dermal tissue layer 10, as shown in FIG. 23, a mixture of extracellular matrix components 11 and dermal cells 12 is poured into the culturing space 45 of the culture tank 41. The mixture is poured in an amount that reaches a height causing the wires 43 to be submerged therein.

Figure 24:
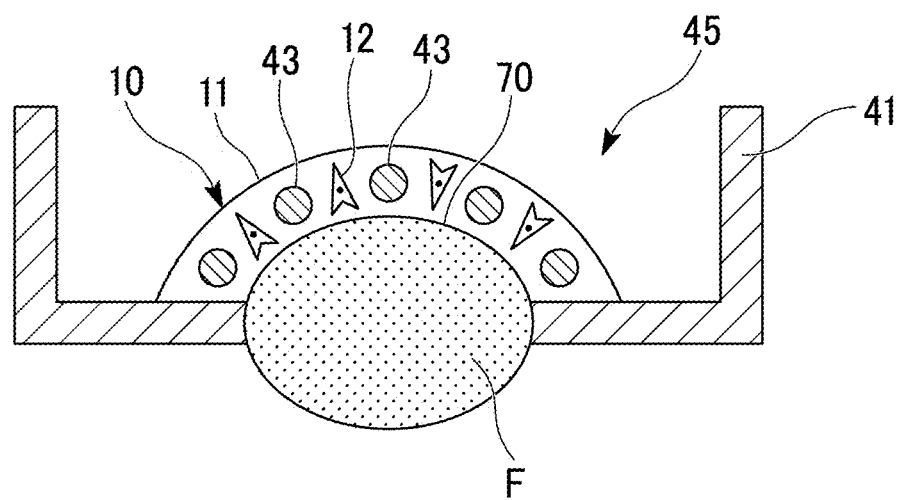
FIG. 24 is a diagram showing the production procedure of an artificial skin tissue 1 according to the second embodiment.

When the mixture of extracellular matrix components 11 and dermal cells 12 is poured into the culture tank 41, the mixture is cultured under predetermined conditions. Since the cultured mixture of extracellular matrix components 11 and dermal cells 12 is such that shrinkage in the direction in which the wires 43 are suspended is suppressed, while shrinkage occurs in other directions, a dermal tissue layer 10 having a shape conforming to the curved surface 70 is formed as shown in FIG. 24.

Figure 25:
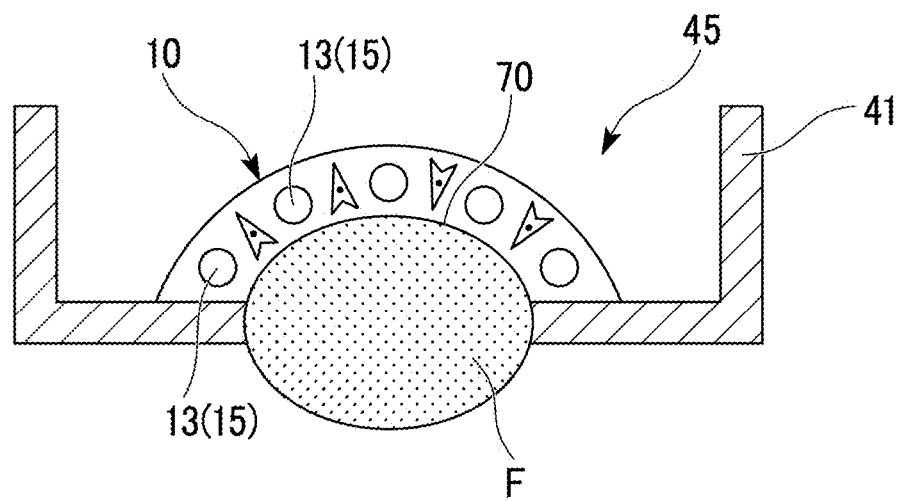
FIG. 25 is a diagram showing the production procedure of an artificial skin tissue 1 according to the second embodiment.
Figure 26:
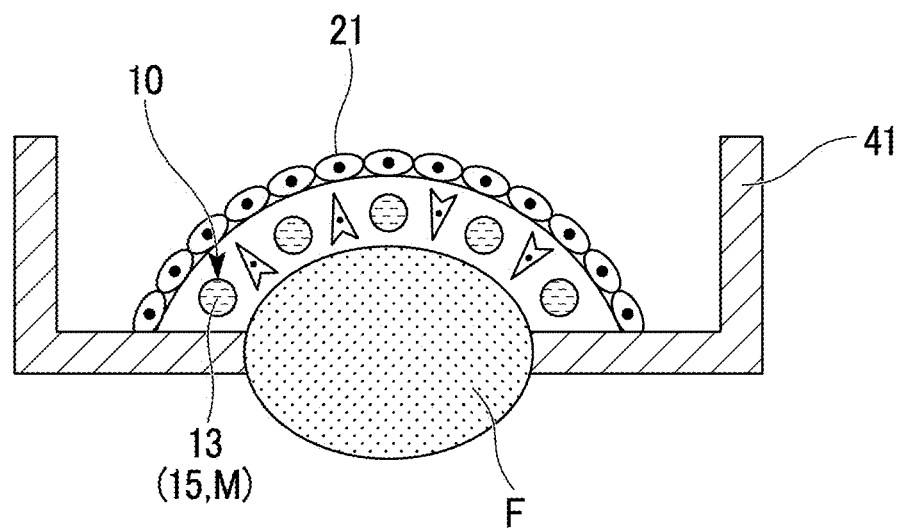
FIG. 26 is a diagram showing the production procedure of an artificial skin tissue 1 according to the second embodiment.

Next, a plurality (five in the present embodiment) of perfusion flow channels 13 is formed in the dermal tissue layer 10 as shown in FIG. 25, by removing the wires 43. Subsequently, vascular cells 14 are poured (inoculated) on the surface of the dermal tissue layer 10 that faces the perfusion flow channels 13 and are cultured for a certain time, and thereby a lumen layer 15 is formed.

Figure 27:
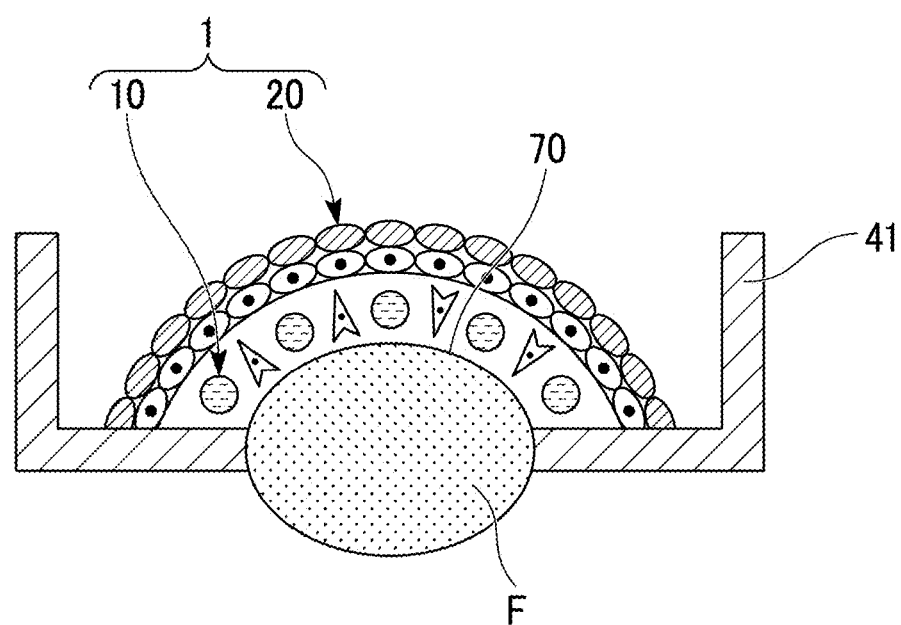
FIG. 27 is a diagram showing the production procedure of an artificial skin tissue 1 according to the second embodiment.

Next, epidermal cells 21 are inoculated on the dermal tissue layer 10. When the epidermal cells 21 are inoculated, the epidermal cells 21 are subjected to gas-liquid culture while a medium M is perfused to the perfusion flow channels 13. Thereby, as shown in FIG. 27, the epidermal cells 21 undergo induced differentiation, and an epidermal layer 20 can be formed. In the present embodiment, an artificial skin tissue 1 in which the dermal tissue layer 10 and the epidermal layer 20 have a curved shape conforming to the curved surface 70 can be obtained.

As such, in the present embodiment, the same function and effects as those in the case of using the perfusion device 40 of the first embodiment can be obtained, and also, a high quality artificial skin tissue 1 having a shape conforming to the curved surface 70 of a biological model F can be easily produced. Therefore, in the present embodiment, a high quality artificial skin tissue 1 having the shape of a desired site can be easily obtained by preparing and using a biological model F for a desired site.

Thus, preferred embodiments of the invention have been described above; however, the invention is not intended to be limited to such particular embodiments, and various alterations and modifications can be made within the scope of the gist of the invention described in the claims.

For example, the embodiments described above have been described by taking the finger skin tissue as an example of the artificial skin tissue 1; however, as described above, the invention is also applicable when the skin tissues of other sites are produced artificially.

Furthermore, the embodiments described above have been described by taking an $O_2$ plasma treatment as an example of the lyophilic treatment for the engaging portions 42c; however, the treatment is not intended to be limited to this, and other lyophilic treatments may also be employed. As a method for increasing the adhesiveness of the mixture of extracellular matrix components 11 and dermal cells 12 to the engaging portions 42c, for example, an adhesive for skin may be used instead of a lyophilic treatment. In the case of using an adhesive for skin, it is preferable to select a material that does not adversely affect extracellular matrix components 11 and dermal cells 12.

The embodiments described above have been described on the basis of a configuration of using wires 43, which are linear members, as the flow channel-forming members for forming the perfusion flow channels 13; however, a configuration of using cell-attached or cell-containing fibers 3 produced from a gel material or a polymer instead of the wires 43, may also be employed. When this configuration is employed, and for example, flow channel-forming members containing vascular cells 14 as cells are used, there is no need to separately provide a process of introducing vascular cells 14, and the production efficiency can be enhanced. Regarding the perfusion flow channel 13, the configuration is not limited to a configuration having linear perfusion flow channels. For example, planar perfusion flow channels can also be formed by using planar members as the flow channel-forming members. In this case, since the flow rate of the medium to be perfused can be increased, and the nutrient supply efficiency can be increased, an artificial skin tissue of superior quality can be produced. Regarding the planar flow channel-forming members, for example, a mesh material can be used.

The embodiments described above have been described on the basis of a configuration of using perfusion flow channels 13 in order to perfuse a medium for culturing epidermal cells 21 and forming an epidermal layer 20; however, the invention is not intended to be limited to this configuration. For example, a configuration in which a drug is applied on the tissue surface (for example, epidermal layer 20), and the perfusion flow channels 13 are used in order to evaluate incorporation of the drug into the perfusion flow channels 13, may also be employed. Furthermore, a configuration in which a drug is mixed into the medium that flows through the perfusion flow channels 13, and the perfusion flow channels 13 are used in order to evaluate diffusion of the drug from the perfusion flow channels 13 to the dermal tissue layer 10 or the epidermal layer 20, may also be employed. In a case in which the perfusion flow channels 13 are used in such a configuration, it is not necessary to form the perfusion flow channels 13 before the epidermal layer 20 is formed, and a procedure of forming the perfusion flow channels 13 after the epidermal layer 20 is formed is also acceptable. Furthermore, in a case in which, for example, only the dermal tissue layer 10 is taken as the object of evaluation, it is not necessary to form the epidermal layer 20.

The embodiments described above have been described on the basis of the artificial skin tissue 1 as the three-dimensional artificial tissue; however, the invention is not intended to be limited to this. The three-dimensional artificial tissue may be, for example, a muscle tissue using skeletal muscle cells or cardiac muscle cells instead of the fibroblasts described above. Furthermore, the three-dimensional artificial tissue may also be a hepatic tissue using hepatic cells, a pancreatic tissue using pancreatic cells, or a nervous tissue using neural cells. In a case in which the invention is applied to such a tissue, the presence of the extracellular matrix used in the above-described embodiments is not necessarily essential, and accumulation of various cells only is also acceptable.

INDUSTRIAL APPLICABILITY

According to the invention, a high quality three-dimensional artificial tissue, a method for producing the same, a three-dimensional artificial tissue perfusion device, and a method for evaluating a drug using a three-dimensional artificial tissue can be provided. Therefore, the present invention is useful in, for example, the fields of cosmetics, medicine, and pharmaceuticals.

REFERENCE SIGNS LIST

1 Artificial skin tissue (three-dimensional artificial tissue)
10 Dermal tissue layer
11 Extracellular matrix components
12 Dermal cells (fibroblasts)
13 Perfusion flow channel
14 Vascular cells
15 Lumen layer
20 Epidermal layer
21 Epidermal cells
40, 40A Perfusion device (three-dimensional artificial tissue perfusion device)
41 Culture tank
42 Connector (supporting portion)
42a Mounting portion (cylindrical portion)
42c Engaging portion
42e Second cylinder
42f Rib portion
43 Wire (linear member, flow channel-forming member)
44 Sidewall
45 Culturing space
46 Bottom wall (bottom)
70 Curved surface
F Biological model
M Medium

What is claimed is:

1. A three-dimensional artificial tissue perfusion device that perfuses to a three-dimensional artificial tissue extending in a predetermined direction, the device comprising:
a culture tank comprising a culturing space surrounded by a plurality of sidewalls;
a flow channel-forming member penetrating through a first sidewall and a second sidewall of the plurality of sidewalls and being suspended in the culturing space along the predetermined direction;
a supporting portion comprising a through-hole which the flow channel-forming member is inserted, being mounted on the first sidewall and the second sidewall of the plurality of sidewalls, penetrating through the first sidewall and the second sidewalls, being connectable to a pipe which a medium is supplied to or a pipe which the medium is discharged at an external side of the culture tank, and supporting the flow channel-forming member in a freely attachable and detachable manner in the culturing space;
wherein the supporting portion has a cylindrical portion comprising the through-hole and being mounted so as to penetrate through the first sidewall and the second sidewall, and an engaging portion provided at the cylindrical portion, and being disposed on a culturing space side of the cylindrical portion,
the engaging portion includes a second cylindrical portion coaxially disposed around an outer circumferential surface of the cylindrical portion, and having an outer circumferential surface and an inner circumferential surface which has a diameter bigger than a diameter of the outer circumferential surface of the cylindrical portion, and
a plurality of rib portions disposed at an interval in a circumferential direction of the cylindrical portion, and connecting the outer circumferential surface of the cylindrical portion and the inner circumferential surface of the second cylindrical portion,
the second cylindrical portion and the plurality of rib portions face the first sidewall and the second sidewall of the plurality of sidewalls at an opposite side of a center of the culturing space through the culturing space, and
the second cylindrical portion and the plurality of rib portions facing the first sidewall and the second sidewall of the plurality of sidewalls through the culturing space are engaged with a portion of the three-dimensional artificial tissue.

2. The three-dimensional artificial tissue perfusion device according to claim 1,
wherein a flow path direction of a perfusion flow path which penetrating the three-dimensional artificial tissue, and being formed by removing the flow path forming member from the three-dimensional artificial tissue is cultured in the culture space and which the flow path forming member penetrates.

3. The three-dimensional artificial tissue perfusion device according to claim 2,
wherein in the supporting portion, at least a region that is exposed to the culturing is subjected to a lyophilic treatment for extracellular matrix components.

4. The three-dimensional artificial tissue perfusion device according to claim 1,
wherein a curved surface extending in the predetermined direction is provided at the bottom of the culture tank, and
the three-dimensional artificial tissue is disposed on the curved surface.

5. The three-dimensional artificial tissue perfusion device according to claim 4,
wherein the curved surface is a part of a biological model.

* * * * *